US012685502B2

(12) United States Patent
Chen et al.

(10) Patent No.: US 12,685,502 B2
(45) Date of Patent: Jul. 21, 2026

(54) METHOD AND DEVICE OF DETECTING BONE MINERAL DENSITY BASED ON LOW DOSE COMPUTED TOMOGRAPHY IMAGE OF CHEST

(71) Applicant: TAIPEI MEDICAL UNIVERSITY, Taipei City (TW)

(72) Inventors: Cheng-Yu Chen, Taipei City (TW); Duen-Pang Kuo, Taipei City (TW); David Carroll Chen, Taipei City (TW)

(73) Assignee: TAIPEI MEDICAL UNIVERSITY, Taipei City (TW)

( * ) Notice: Subject to any disclaimer, the term of this patent is extended or adjusted under 35 U.S.C. 154(b) by 526 days.

(21) Appl. No.: 18/335,970

(22) Filed: Jun. 15, 2023

(65) Prior Publication Data

US 2024/0415479 A1 Dec. 19, 2024

(51) Int. Cl.
*A61B 6/03* (2006.01)
*A61B 6/50* (2024.01)
*G06T 7/00* (2017.01)

(52) U.S. Cl.
CPC .............. *A61B 6/505* (2013.01); *A61B 6/035* (2013.01); *G06T 7/0012* (2013.01); *G06T 2207/30012* (2013.01)

(58) Field of Classification Search
None
See application file for complete search history.

(56) References Cited

U.S. PATENT DOCUMENTS 5,915,036 A * 6/1999 Grunkin ................ G06T 7/0012
382/280
10,039,513 B2 * 8/2018 Bregman-Amitai ... A61B 6/481
(Continued)

FOREIGN PATENT DOCUMENTS

CN 111932559 * 11/2020 .............. G06T 7/11
CN 112074841 A 12/2020
(Continued)

OTHER PUBLICATIONS

Chen, YC., Li, YT., Kuo, PC. et al. Automatic segmentation and radiomic texture analysis for osteoporosis screening using chest low-dose computed tomography. Eur Radiol 33, 5097-5106 (2023). https://doi.org/10.1007/s00330-023-09421-6 (Year: 2023).*
Cheng Y, Yang H, Hai Y, Pan A, Zhang Y and Zhou L (2022) Hounsfield unit for assessing asymmetrical loss of vertebral bone mineral density and its correlation with curve severity in adolescent idiopathic scoliosis. Front. Surg. 9:1000031. doi: 10.3389/fsurg.2022.1000031 (Year: 2022).*
(Continued)

*Primary Examiner* — Beniyam Menberu
(74) *Attorney, Agent, or Firm* — IDEA Intellectual Limited; Sam T. Yip

(57) ABSTRACT

Disclosed are methods and devices of processing a low-dose computed tomography (CT) image. The present disclosure provides a method of processing a low-dose computed tomography (LDCT) image. The method includes receiving a first set of chest images, the first set of chest images generated by a low-dose CT method; determining a vertebral body region in each image of the first set of chest images; determining an anterior part within each vertebral body region; obtaining a first set of features from the anterior parts of the first set of chest images; selecting a second set of features from the first set of features; and determining whether a bone mineral density of the vertebral body regions is abnormal based on the second set of features.

19 Claims, 11 Drawing Sheets

(56) References Cited

U.S. PATENT DOCUMENTS

| | | | | |
|---|---|---|---|---|
| 2002/0009215 A1* | 1/2002 | Armato, III | ............ | G06T 7/187 |
| | | | | 382/131 |
| 2016/0015347 A1* | 1/2016 | Bregman-Amitai | ......................... | |
| | | | | G06T 7/0012 |
| | | | | 382/131 |
| 2019/0021677 A1 | 1/2019 | Grbic et al. | | |
| 2019/0336097 A1* | 11/2019 | Bregman-Amitai | ... | A61B 6/505 |
| 2021/0212647 A1 | 7/2021 | Zheng et al. | | |
| 2022/0148164 A1 | 5/2022 | Hassanpour et al. | | |
| 2022/0318996 A1* | 10/2022 | Wang | .................... | G06T 7/0012 |
| 2023/0029674 A1* | 2/2023 | Lin | ......................... | A61B 6/469 |
| 2025/0173860 A1* | 5/2025 | Gawel | ....................... | G06T 7/62 |

FOREIGN PATENT DOCUMENTS

| | | | | | | |
|---|---|---|---|---|---|---|
| CN | 114092466 | | * | 2/2022 | .............. | G06N 3/04 |
| CN | 115690063 | A | | 2/2023 | | |
| CN | 115886853 | A | | 4/2023 | | |
| JP | 2007312892 | | * | 12/2007 | .............. | A61B 6/03 |
| WO | 2016013004 | A1 | | 1/2016 | | |
| WO | WO 2022126903 | | * | 6/2022 | .............. | G06T 7/00 |

OTHER PUBLICATIONS

Yung-Chieh Chen et al., "Automatic segmentation and radiomic texture analysis for osteoporosis screening using chest low-dose computed tomography", European Radiology, 2023, pp. 1-10.

Office Action of corresponding Taiwan patent application No. 112122347 mailed on Jan. 3, 2024.

International Search Report and Written Opinion of corresponding PCT Patent Application No. PCT/US2023/072342 mailed on Nov. 15, 2023.

Yung Chieh Chen et al., "Automatic segmentation and radiomic texture analysis for osteoporosis screening using chest low dose computed tomography", European Radiology, Springer, Jan. 2023.

Yaling Pan et al., "Automatic opportunistic osteoporosis screening using low-dose chest computed tomography scans obtained for lung cancer screening", European Radiology, Springer, Feb. 2020, vol. 30, pp. 4107-4116.

Uran Ferizi et al., "Artificial Intelligence, Osteoporosis and Fragility Fractures", Curr Opin Rheumatol, Jul. 2019, vol. 31, No. 4, pp. 368-375.

Office Action of the corresponding Taiwan patent application No. 112122347 mailed on Apr. 21, 2025.

* cited by examiner

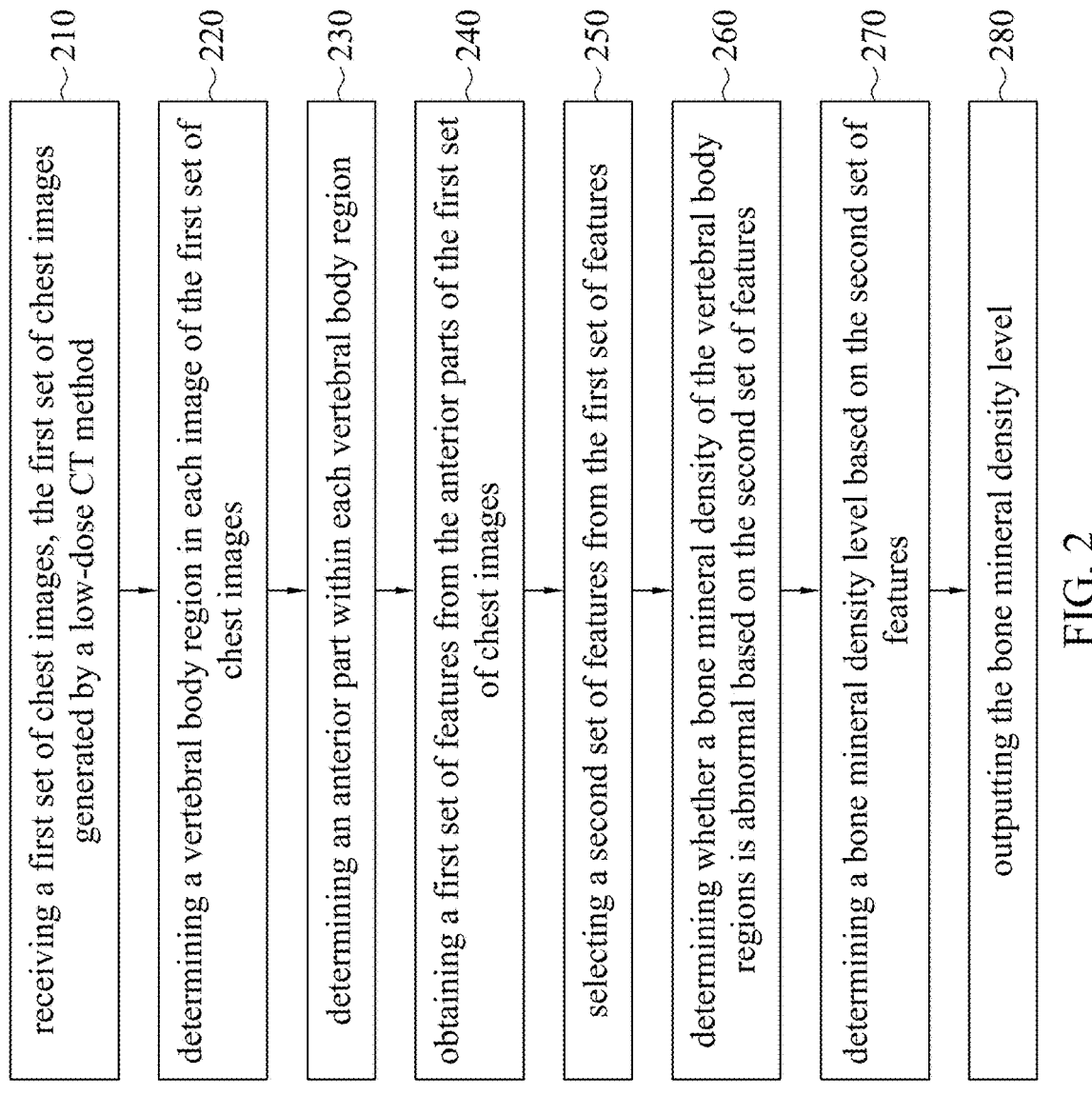

2000 receiving a first set of chest images, the first set of chest images generated by a low-dose CT method ~210 determining a vertebral body region in each image of the first set of chest images ~220 determining an anterior part within each vertebral body region ~230 obtaining a first set of features from the anterior parts of the first set of chest images ~240 selecting a second set of features from the first set of features ~250 determining whether a bone mineral density of the vertebral body regions is abnormal based on the second set of features ~260 determining a bone mineral density level based on the second set of features ~270 outputting the bone mineral density level ~280

FIG. 2

3000 receiving a first set of chest images, the first set of chest images generated by a low-dose CT method ~310 determining a vertebral body region in each image of the first set of chest images ~320 determining an anterior part within each vertebral body region ~330 obtaining a first set of features from the anterior parts of the first set of chest images ~340 selecting a second set of features from the first set of features ~350 obtaining a selected set of chest images from the second set of features ~360 determining whether a bone mineral density of the vertebral body regions is abnormal based on the selected set of chest images ~370 determining a bone mineral density level based on the selected set of chest images ~380 outputting the bone mineral density level ~390

FIG. 3

VertebralBody

Tissue

Background

Lung

VertebralBody

Tissue

Background

Lung 2000A  2001A

2100A 2000B  2001B

2100B 2000C  2001C

2100C

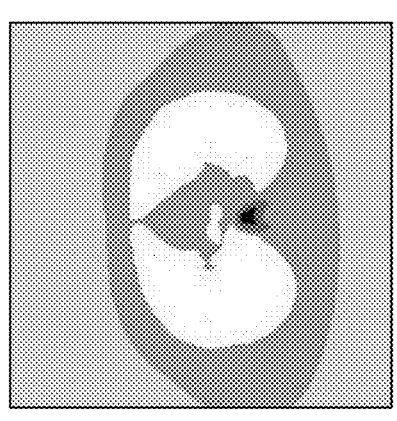
FIG. 10C
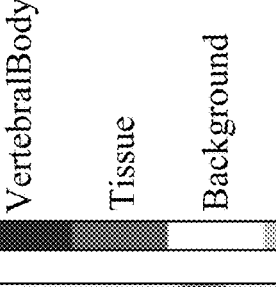
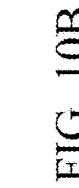
VertebralBody
Tissue
Background
Lung
FIG. 10B
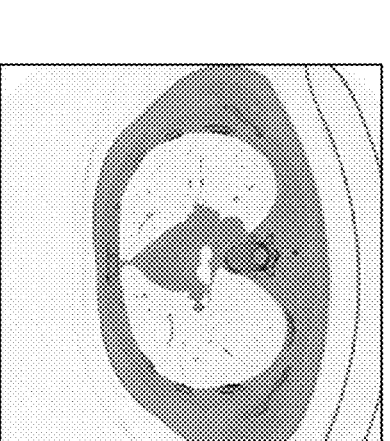
FIG. 10A

METHOD AND DEVICE OF DETECTING BONE MINERAL DENSITY BASED ON LOW DOSE COMPUTED TOMOGRAPHY IMAGE OF CHEST

FIELD OF THE INVENTION

The present disclosure relates to a method of processing low-dose computed tomography (CT) images and related devices. In particular, the present disclosure relates to methods of processing low-dose CT images to determine a bone mineral density of the bone region, and to related devices.

BACKGROUND

Medical advances have extended life expectancy, increasing the importance of maintaining health. Regular health examinations are critical to detect possible health problems at the earliest possible stage. Summary of the Invention The present disclosure provides a method of processing low-dose computed tomography (LDCT) chest images. The method includes receiving a first set of chest images, the first set of chest images generated by a low-dose CT method; determining a vertebral body region in each image of the first set of chest images; determining an anterior part within each vertebral body region; obtaining a first set of features from the anterior parts of the first set of chest images; selecting a second set of features from the first set of features; and determining whether a bone mineral density of the vertebral body regions is abnormal based on the second set of features.

According to another embodiment, the present disclosure provides a device of processing low-dose computed tomography (LDCT) chest images. The device includes a processor and a memory coupled with the processor. The processor executes computer-readable instructions stored in the memory to perform operations. The operations include receiving a first set of chest images, the first set of chest images generated by a low-dose CT method; determining a vertebral body region in each image of the first set of chest images; determining an anterior part within each vertebral body region; obtaining a first set of features from the anterior parts of the first set of chest images; selecting a second set of features from the first set of features; and determining whether a bone mineral density of the vertebral body regions is abnormal based on the second set of features. In a clinical environment, the low-dose computed tomography (LDCT) and dual-energy x-ray absorptiometry (DXA) are two different and independent detection techniques. The LDCT is used to examine the lungs, and the DXA is used to examine the bone mineral density (BMD).

The object of the present disclosure is to examine the BMD based on the LDCT lung images. In this way, an additional DXA examination for the BDM can be omitted. That is, the present disclosure can use the LDCT to image the lungs and evaluate the bone mineral density at the same time. Therefore, for those patients whose BMD needs to be examined in addition to the LDCT lung images, the radiation dose implied to the patients can be reduced since the DXA can be omitted.

BRIEF DESCRIPTION OF THE DRAWINGS

In order to describe the manner in which advantages and features of the present disclosure can be obtained, a description of the present disclosure is rendered by reference to specific embodiments thereof, which are illustrated in the appended drawings. These drawings depict only example embodiments of the present disclosure and are not therefore to be considered limiting its scope.

FIG. 2 is a flowchart of a method of processing a low-dose CT image, in accordance with some embodiments.

FIG. 3 is a flowchart of a method of processing a low-dose CT) image, in accordance with some embodiments.

FIGS. 10A, 10B, and 10C show low-dose CT images, in accordance with some embodiments.

DETAILED DESCRIPTION

Figure 1A:
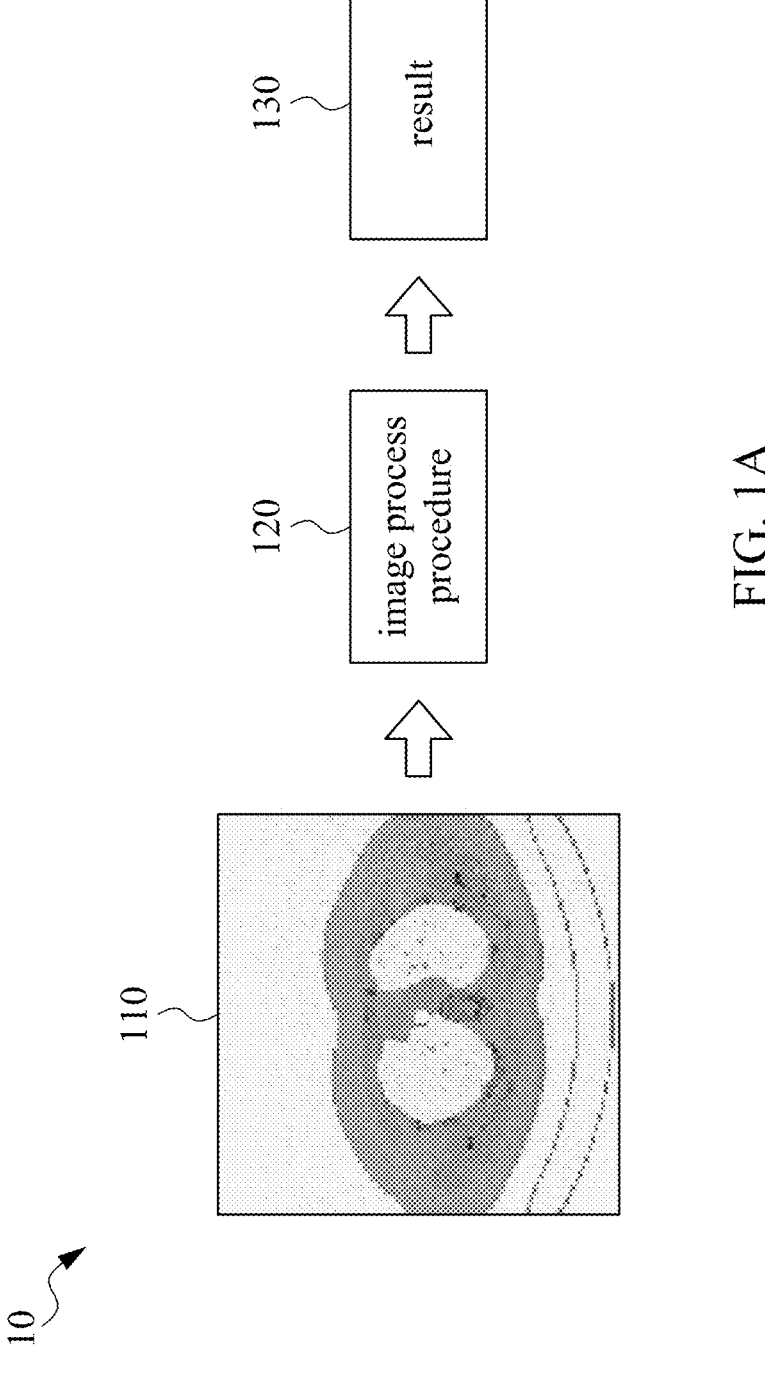
FIG. 1A is a diagram of a CT image processing architecture, in accordance with some embodiments of the present disclosure.

The following disclosure provides many different embodiments, or examples, for implementing different features of the provided subject matter. Specific examples of operations, components, and arrangements are described below to simplify the present disclosure. These are, of course, merely examples and are not intended to be limiting. For example, a first operation performed before or after a second operation in the description may include embodiments in which the first and second operations are performed together, and may also include embodiments in which additional operations may be performed between the first and second operations. For example, the formation of a first feature over, on or in a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Time relative terms, such as "prior to," "before," "posterior to," "after" and the like, may be used herein for ease of description to describe the relationship of one operation or feature to another operation(s) or feature(s) as illustrated in the figures. The time relative terms are intended to encompass different sequences of the operations depicted in the figures. Further, spatially relative terms, such as "beneath," "below," "lower," "above," "upper" and the like, may be used herein for ease of description to describe the relationship of one element or feature to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly. Relative terms for connections, such as "connect," "connected," "connection," "couple," "coupled," "in communication," and the like, may be used herein for ease of description to describe an operational connection, coupling, or linking one between two elements or features. The relative terms for connections are intended to encompass different connections, coupling, or linking of the devices or components. The devices or components may be directly or indirectly connected, coupled, or linked to one another through, for example, another set of components. The devices or components may be wired and/or wirelessly connected, coupled, or linked with each other.

As used herein, the singular terms "a," "an," and "the" may include plural referents unless the context clearly indicates otherwise. For example, reference to a device may include multiple devices unless the context clearly indicates otherwise. The terms "comprising" and "including" may indicate the existences of the described features, integers, steps, operations, elements, and/or components, but may not exclude the existences of combinations of one or more of the features, integers, steps, operations, elements, and/or components. The term "and/or" may include any or all combinations of one or more listed items.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified.

The nature and use of the embodiments are discussed in detail as follows. It should be appreciated, however, that the present disclosure provides many applicable inventive concepts that can be embodied in a wide variety of specific contexts. The specific embodiments discussed are merely illustrative of specific ways to embody and use the disclosure, without limiting the scope thereof.

FIG. 1A is a diagram of CT image processing architecture 10, in accordance with some embodiments of the present disclosure. The CT image processing architecture 10 includes one or more CT images 110, an image process model 120, and a result 130.

The CT image 110 can be a full-dose CT image or a low-dose CT image. In some embodiments, the CT image 110 can be a chest CT image of a human. In some embodiments, the CT image 110 can be a thoracic CT image of a human. The low-dose CT method can be less physically harmful than other methods due to the lower radiation. The CT image 110 can show one or more organs of a human. In some embodiments, the CT image 110 can show lungs, heart, or, bone regions (such as thoracic vertebrae or a vertebral body region). In some embodiments, the vertebral body region can include a thoracic spine, vertebral body, intervertebral disc, cortical bone, basivertebral vein, endplate, and trabecular bone. In some embodiments, the CT image 110 can be a two-dimensional (2D) image. In other embodiments, the CT image 110 can be a three-dimensional (3D) image.

The one or more CT images 110 can be input to the image process procedure 120. In some embodiments, the image process procedure 120 can include one or more models therein. For example, the image process procedure 120 can include, but is not limited to, object detection, semantic segmentation, classification, and localization models. In some embodiments, the image process procedure 120 can analyze pixels in the CT image 110. The image process procedure 120 can detect each element in the CT image 110. In some embodiments, the image process procedure 120 can analyze different organs in the CT image 110.

The image process procedure 120 can output the result 130. The result 130 may be "normal" or "abnormal." The result 130 may be "normal," "osteopenia," or "osteoporosis." The processed image 110 can be processed through different models. Characteristics of the organs or tissues can be analyzed to ascertain the condition thereof.

Figure 1B:
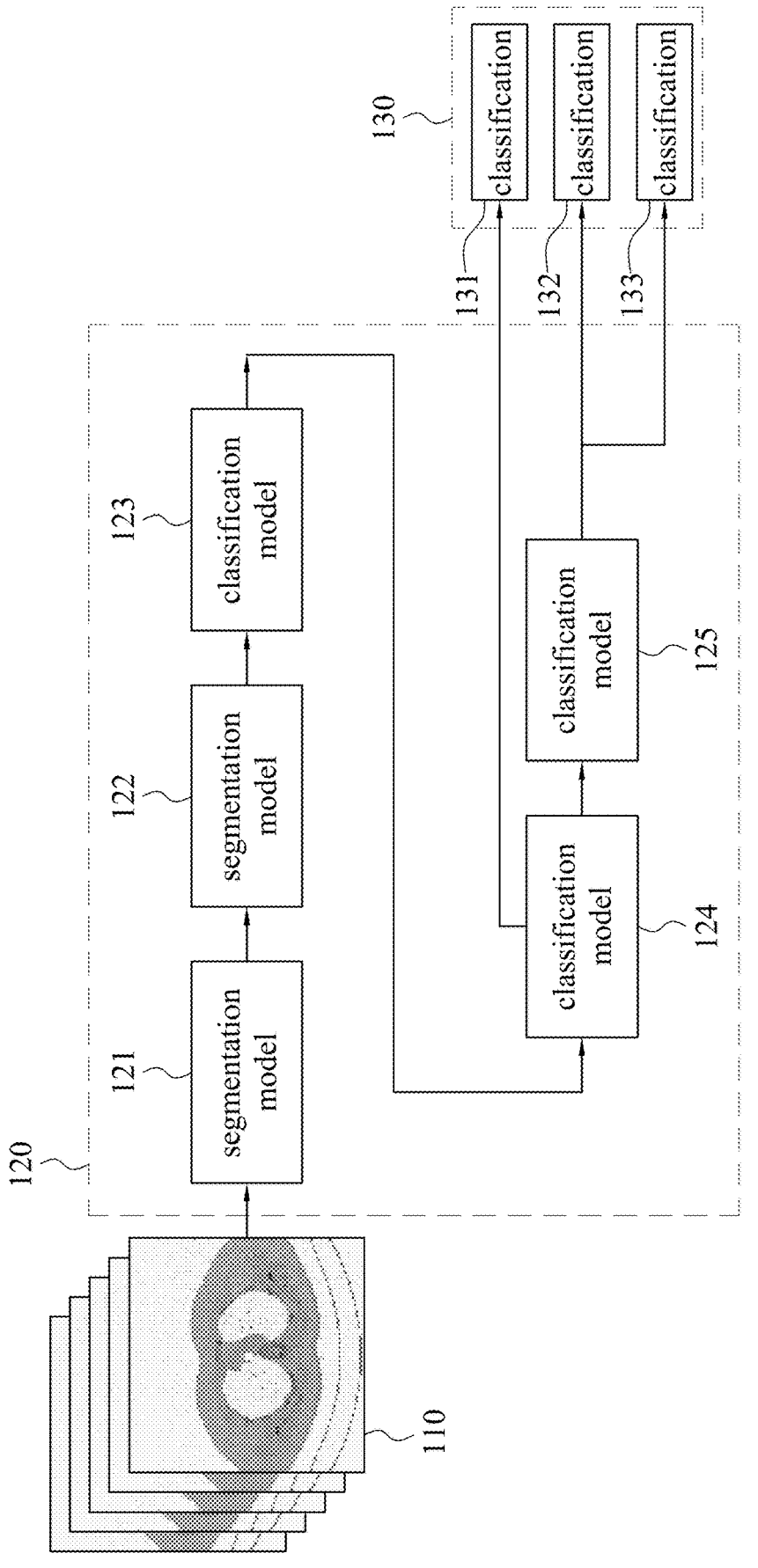
FIG. 1B is a diagram of a CT image processing architecture, in accordance with some embodiments of the present disclosure.

FIG. 1B is a diagram of CT image processing architecture 10', in accordance with some embodiments of the present disclosure. The CT image processing architecture 10' includes one or more CT images 110, an image process procedure 120, and a result 130.

The one or more CT images 110 can be a full-dose CT images or a low-dose CT images. The one or more CT images 110 can be chest CT images of a human. The one or more CT images 110 can be thoracic CT images of a human. The CT images 110 can show lungs, heart, or, bone regions (such as thoracic vertebrae or a vertebral body region). In some embodiments, the vertebral body region can include a thoracic spine, vertebral body, intervertebral disc, cortical bone, basivertebral vein, endplate, and trabecular bone. The CT images 110 can be a two-dimensional (2D) images or three-dimensional (3D) images.

The images obtained a low-dose CT method can be less physically harmful than other methods due to the lower radiation. However, since the characteristics of the low-dose CT method, the noises in the CT images would be obviously high. Therefore, the subject disclosure provides a novel and inventive procedure for processing the low-dose CT images. Through the novel and inventive procedure of the subject disclosure the prediction or detection of the bone mineral density with good accuracy can be obtained.

The one or more CT images 110 can be input to the image process procedure 120 for further processes. In some embodiments, the image process procedure 120 can include one or more models therein. As shown, the image process procedure 120 can include, but is not limited to, segmentation models 121 and 122 and classification model 123, 124, and 125.

The segmentation model 121 may be applied on the CT images 110 to obtain several semantic segmentations in each CT image 110. For example, after application of the segmentation model 121, four semantic segmentations may be obtained in each CT image 110, and these four semantic segmentations includes the background, soft tissues (e.g., fat tissue or muscle tissue), lung, and vertebral body. The segmentation model 121 may include FCN (Fully Convolutional Network), DeconvNet (Deconvolution Network), U-Net, SegNet, DeepLab, RefineNet, and PSPNet (Pyramid Scene Parseing Network).

Figure 5C:
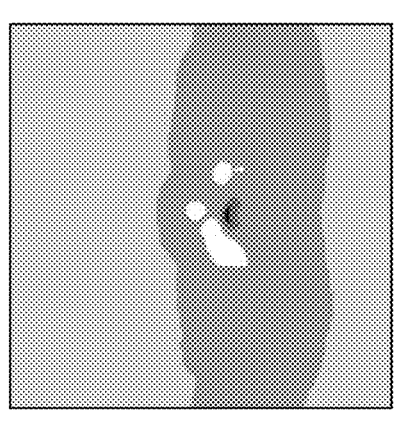
FIGS. 5A, 5B, 5C, 6A, 6B, and 6C show low-dose CT images, in accordance with some embodiments.
Figure 5B:
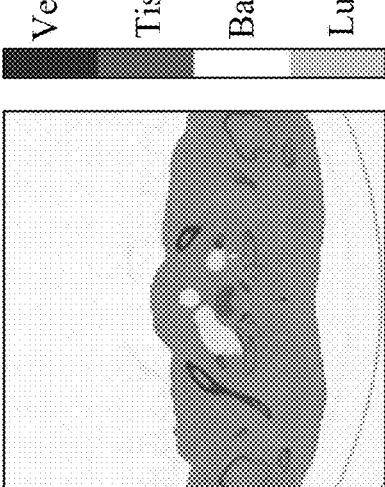
Figure 5A:
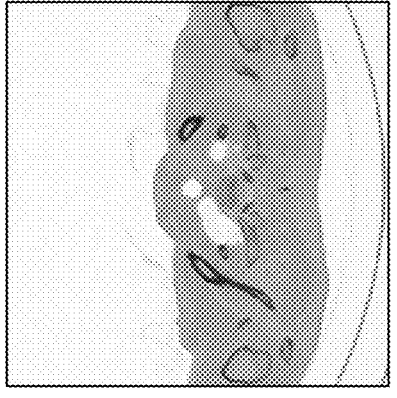
Figure 6C:
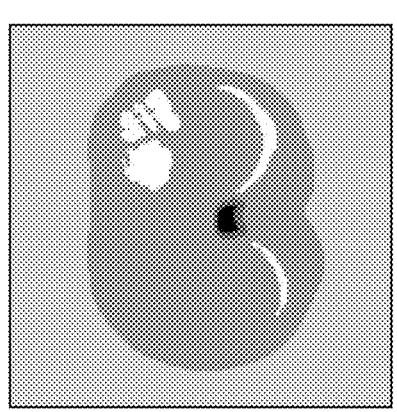
Figure 6B:
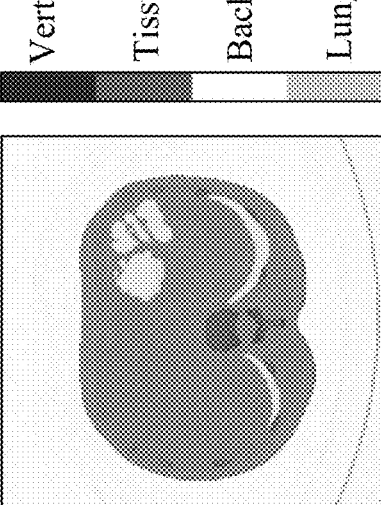
Figure 6A:
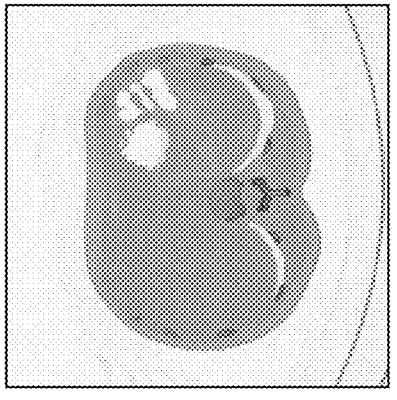

In some embodiments, after the segmentation model 121, the ratio of lung to vertebral body in each CT image 110 can be calculated. Based on the ratio of lung to vertebral body, the CT images 110 at the level of the apical lungs or the diaphragm may be removed (or discarded). In some embodiments, when the ratio of lung to vertebral body in a CT image is smaller than a threshold, the CT image can be removed (or discarded). In some embodiments, the use of the 10th quantile as a threshold is effective for removing unwanted CT images. Since the CT images at the level of the apical lungs or the diaphragm often exhibit increased lordotic curvature of the spine or poor image quality and can lead to suboptimal selection quality, the removal of these CT images would be much helpful to get accurate prediction or detection of the bone mineral density. Furthermore, by discarding or removing the undesired CT images, the noise due to the low-CT method would be smoothed, and the prediction and detection would be more accurate. FIGS. 5A to 5C may be directed to an exemplary CT image at the level of the apical lungs. FIGS. 6A to 6C may be directed to an exemplary CT image at the level of the diaphragm.

The segmentation model 122 may be applied on the CT images 110 including several semantic segmentations (e.g., background region, tissue region, lung region, and vertebral body region). In some embodiments, the segmentation model 122 may be applied on a subset of the CT images 110, in which the CT images at the level of the apical lungs or the diaphragm are removed.

The vertebral body region in each CT images 110 may include thoracic spine, vertebral body, intervertebral disc, cortical bone, basivertebral vein, endplate, and trabecular bone. After the application of the segmentation model 122, an anterior part within the vertebral body of each CT image 110 can be determined. The anterior part of the vertebral body region can include the trabecular bone and exclude the cortical bone and the basivertebral vein. Determination of the anterior part within vertebral body region can be helpful to get accurate prediction or detection of the bone mineral density because the cortical bone and the basivertebral vein are not the tissues or organs to be measured or observed and may influence the accuracy of the prediction or detection of the bone mineral density. Furthermore, by narrowing down to the observed regions, the noise due to the low-CT method would be smoothed, and the prediction and detection would be more accurate.

In some embodiments, the segmentation model 122 may include FCN, DeconvNet, U-Net, SegNet, DeepLab, RefineNet, and PSPNet.

In some embodiments, the segmentation model 122 may determine the anterior part of each CT image 110 by shrinking the area of the vertebral body region. The segmentation model 122 may determine the anterior part of each CT image 110 by shrinking 2 to 3 pixels from the boundary of the area of the vertebral body region.

After the segmentation model 122, a set of feature values from the anterior parts of the CT images 110 can be obtained. The feature value may be any kind of value describing the characteristic of the anterior part. For example, the feature value may be a gray scale value or a radiodensity values of the anterior part. The unit of a radiodensity value may be Hounsfield unit (HU). In some embodiments, one element the set of feature values from the anterior parts of the CT images 110 may be an average of the radiodensity values within the anterior part of one CT image 110.

The classification model 123 can be applied on the set of feature values. After the application classification model 123, a subset of feature values may be determined. The subset of feature values corresponds to the CT images 110 associated with the trabeculae or the trabecular bone. The feature values which are excluded from the subset of feature values may corresponds to the CT images 110 associated with endplates and intervertebral discs. Since the bone mineral densities of the endplates and the intervertebral discs may be different from (e.g., much greater than) those of the trabeculae, the prediction and detection of the bone mineral density including the endplates and the intervertebral discs would be less accurate. Therefore, the CT images including associated with endplates and intervertebral discs should be discarded or removed. Furthermore, by discarding or removing the undesired CT images, the noise due to the low-CT method would be smoothed, and the prediction and detection would be more accurate.

Figures 8A, 8B, 8C:
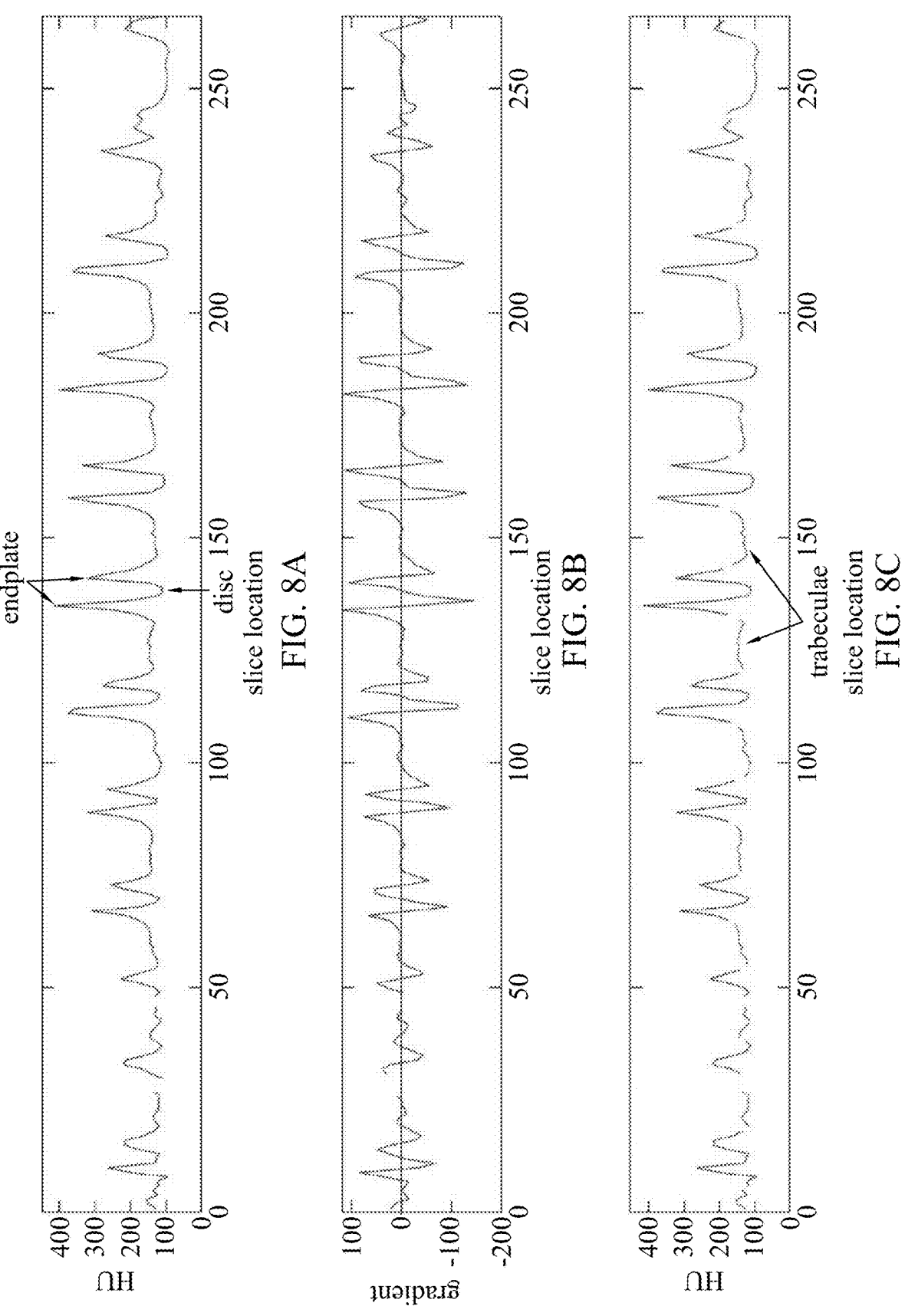
FIGS. 8A, 8B, and 8C are diagrams obtained from the anterior parts of the first set of thoracic images, in accordance with some embodiments.

In some embodiments, the classification model 123 may be applied on the curved graph based on the sequence (or locations) of the CT images 110 versus the set of feature values (e.g., the curved graphs shown in FIGS. 8A and 8C). In some embodiments, the classification model 123 may be applied on the curved graph and the first differential values of the curved graph (e.g., the curved graph shown in FIG. 8B). In some embodiments, the classification model 123 may be applied on the curved graph and the second differential values of the curved graph. In some embodiments, the classification model 123 may be applied on the curved graph and the first and second differential values of the curved graph.

The classification model 123 may include Support Vector Machine (SVM), Decision Tree, Random Forest model, eXtreme Gradient Boosting (XGBoost) model. In some embodiments, the classification model 123 may be an anomaly detection model. The anomaly detection model may include long short term memory autoencoder (LSTM autoencoder), one-class support vector machine (one-class SVM), and isolation forest model.

The classification model 124 may be applied on the subset of the feature values. The classification model 124 may determine, based on the subset of the feature values, whether the corresponding bone mineral density belongs to classification 131 or not. The classification 131 may indicate "normal." When the classification model 124 determine that the corresponding bone mineral density does not belong to classification 131 (i.e., "abnormal"), the classification model 125 may be applied on the subset of the feature values. The classification model 125 may determine, based on the subset of the feature values, if the corresponding bone mineral density belongs to classification 132 or 133. The classification 132 may indicate "osteopenia." The classification 133 may indicate "osteoporosis."

In some embodiments, the classification model 124 may be applied on a subset of the CT images 110 corresponding to the subset of the feature values. The classification model 124 may determine, based on the subset of the CT images 110, whether the corresponding bone mineral density belongs to classification 131 or not. The classification 131 may indicate "normal." When the classification model 124 determine that the corresponding bone mineral density does not belong to classification 131 (i.e., "abnormal"), the classification model 125 may be applied on the subset of the CT images 110. The classification model 125 may determine, based on the subset of the CT images 110, if the corresponding bone mineral density belongs to classification 132 or 133. The classification 132 may indicate "osteopenia." The classification 133 may indicate "osteoporosis."

The classification models 124 and 125 may include Support Vector Machine (SVM), Decision Tree, Random Forest model, eXtreme Gradient Boosting (XGBoost) model.

In some embodiments, the segmentation model 121, segmentation model 122, and segmentation model 123 may be carried out in one segmentation model. After applying the LDCT chest images of one subject (e.g., one patient) to said segmentation model (e.g., including the functions of the segmentation model 121, segmentation model 122, and segmentation model 123), a feature extraction may be performed. Then, a set of features is determined or generated for the subject. Said set of features is then applied to the classification model 124 to determine whether the corresponding bone mineral density belongs to classification 131 or not. The classification 131 may indicate "normal." When the classification model 124 determine that the corresponding bone mineral density does not belong to classification 131 (i.e., "abnormal"), the classification model 125 may be applied on said set of features. The classification model 125 may determine if the corresponding bone mineral density belongs to classification 132 or 133. The classification 132 may indicate "osteopenia." The classification 133 may indicate "osteoporosis."

FIG. 2 is a flowchart of a method 2000 of processing a low-dose CT image, in accordance with some embodiments. The method 2000 can include operations 210, 220, 230, 240, 250, 260, 270, and 280. In some embodiments, this method 2000 can be performed by one or more models. For example, the models can utilize artificial intelligence (AI). In some embodiments, a memory can store instructions, which may be executed by a processor to perform the method 2000.

Referring to FIG. 2, the method 2000 can begin at operation 210, in which one or more low-dose computed tomography (CT) images are received. In the operation 210, a first set of chest images (or thoracic images) are received. The first set of chest images are generated by a low-dose CT method. In some embodiments, the CT image can be generated by computed tomography scan. The first set of chest images may be for one subject or patient and may include 200 LDCT chest images or slices. The CT scan is a medical imaging technique used to obtain detailed internal images of the body. In some embodiments, the CT scanners can utilize a rotating X-ray tube and a row of detectors placed in a gantry to measure X-ray attenuations by different tissues inside the body. The multiple X-ray measurements taken from different angles are then processed on a computer using tomographic reconstruction algorithms to produce tomographic images, or cross-sections (virtual "slices") of a body. In some embodiments, the low-dose CT images in operation 210 can be 2D or 3D images.

Each patient has a set of LDCT chest images (including about 200 slices), which may correspond to the first set of chest images. The semantic segmentation applied to the 200 LDCT chest images may be performed (e.g., through the segmentation model 121 and/or 122). After segmentation, the images which are suitable for feature extraction are automatically selected (e.g., through the classification model 123 or through an algorithm). After selection, for each patient, there are about 40 to 60 LDCT chest images left. The feature extraction is performed for the 40 to 60 LDCT chest images, and a set of feature may be determined, extracted or generated for a patient.

In operation 220, a vertebral body region in each image of the first set of chest images is determined. In some embodiments, the vertebral body region in each of the first set of chest images is determined by a first segmentation model (e.g., the segmentation model 121). In some embodiments, the first segmentation model includes models such as FCN, DeconvNet, U-Net, SegNet, DeepLab, RefineNet, PSPNet, etc. The vertebral body region can include a thoracic spine, vertebral body, intervertebral disc, cortical bone, basivertebral vein, endplate, and trabecular bone.

In some embodiments, the determination of the vertebral body region may be viewed as a pixel-level classification problem. Referring to FIG. 4B, four regions of a chest image may be determined. the determination of the four region of a chest image may be viewed as a four-class pixel-level classification problem. In some embodiments, to address the four-class pixel-level classification problem, a residual convolutional neural network model is employed based on a ResNet50 architecture. Model training or testing was conducted using the Deep Learning Toolbox and Statistics and Machine Learning Toolbox in MATLAB R2021a (Math Works Inc.: Natick, MA, USA) on a single NVIDIA Geforce RTX 2080 Ti GPU (64-GB graphic memory). An experienced radiologist manually labels 30 vertebral body contours across the thoracic vertebrae on 147 LDCT images by using MATLAB's Image Labeler application. The resultant 4410 annotated low-dose CT (LDCT) images were then randomly split into training (n=2670), validation (n=870), and test (n=870) sets.

In some embodiments, a lung region in each image of the first set of chest images is determined. For each image of the first set of chest images, a ratio of an area of the lung region to the whole image is determined and then some of the images from the first set of chest images are discarded, each of which has a ratio smaller than a threshold. In some embodiments, for each image of the first set of chest images, a ratio of an area of the lung region to an area of vertebral body region is determined and then some of the images from the first set of chest images are discarded, each of which has a ratio smaller than a threshold. The discarded chest images may be at the level of the apical lungs or the diaphragm. Since the CT images (or slices) at the level of the apical lungs or the diaphragm often exhibit increased lordotic curvature of the spine or poor image quality and can lead to suboptimal selection quality, the removal of these CT images would be much helpful to get accurate prediction or detection of the bone mineral density. Furthermore, by discarding or removing the undesired CT images, the noise due to the low-CT method would be smoothed, and the prediction and detection would be more accurate. FIGS. 5A to 5C may be directed to an exemplary CT image at the level of the apical lungs. FIGS. 6A to 6C may be directed to an exemplary CT image at the level of the diaphragm.

The semantic segmentation image is generated through the first segmentation model. The semantic segmentation image may include lungs region (or area), the vertebral body (VB) region (or area), and heart and other soft tissues region (or area).

In operation 230, an anterior part of each vertebral body region is determined. An anterior part of the vertebral body is further defined or determined by the anterior ½ to ¾ of the vertebral body. In this way, the basivertebral veins and the cortical bone can be avoided or excluded. The anterior part of the vertebral body region can include the trabecular bone. Determination of the anterior part within vertebral body region can be helpful to get accurate prediction or detection of the bone mineral density because the cortical bone and the basivertebral vein are not the tissues or organs to be measured or observed and may influence the accuracy of the prediction or detection of the bone mineral density. Furthermore, by narrowing down to the observed regions, the noise due to the low-CT method would be smoothed, and the prediction and detection would be more accurate.

In some embodiments, the anterior part of the vertebral body region is determined by a second segmentation model (e.g., the segmentation model 122). The second segmentation model includes models such as FCN, DeconvNet, U-Net, SegNet, DeepLab, RefineNet, and PSPNet, etc. In some embodiments, the anterior part of the vertebral body region includes a trabecular bone. In some embodiments, the anterior part of the vertebral body region does not include cortical bone or basivertebral vein. In some embodiments, the anterior part of the vertebral body region may be determined by reducing an area of the vertebral body region in each of the first set of chest images. In some embodiments, reducing the area of the vertebral body region in each of the first set of chest images comprises reducing 2 to 3 pixels from the boundary of the area of the vertebral body region.

In operation 240, a first set of features are obtained from the anterior parts of the first set of chest images. The first set of features correspond to the radiodensity. The first set of features may correspond to a curved graph. The curved graph is determined based on a sequence (or locations) of the first set of chest images versus the first set of features of the anterior parts of the vertebral body regions of the first set of chest images. The radiodensity can be presented in Hounsfield unit (HU), which may be frequently used in CT scans. The Hounsfield unit of different material can be different. According to the different HU, it can be determined whether the bone region HU is in a normal range. In some embodiments, the bone mineral density of the vertebral body regions can be determined based on the HU of the bone regions.

In operation 250, a second set of features are selected from the first set of features. In some embodiments, the second set of features is selected by an anomaly detection mode (e.g., the classification model 123) or an third classification model (e.g., the classification model 123). The anomaly detection mode includes a LSTM autoencoder, one-class SVM, and isolation forest model. The third classification model includes a SVM, Decision Tree, Random Forest model, and XGBoost model.

In some embodiments, the second set of features is selected based on the first differential values, the gradient values (e.g., FIG. 8B), or the second differential values of the curved graph (e.g., FIG. 8A or 8C), which is generated based on the first set of features. In some embodiments, the second set of features correspond to the anterior parts including a trabecular bone. The second set of features may correspond to the anterior parts excluding endplates and intervertebral discs.

In some embodiments, the second set of chest images corresponding to the second set of features can be selected from the first set of chest images. The second set of chest images selected from the first set of chest images exclude the images having an endplate and/or an intervertebral disc.

Since the bone mineral densities of the endplates and intervertebral discs are different from (e.g., much greater than) those of the trabeculae, the prediction and detection of the bone mineral density including the endplates and the intervertebral discs would be less accurate. Therefore, the CT images including associated with endplates and intervertebral discs should be discarded or removed. Furthermore, by discarding or removing the undesired CT images, the noise due to the low-CT method would be smoothed, and the prediction and detection would be more accurate.

The operation 260 determines whether a bone mineral density of the vertebral body regions is abnormal based on the second set of features. The feature extraction can be used to determine whether the bone mineral density of the vertebral body regions is normal or abnormal (e.g., through the classification models 124 and 125). In some embodiments, determination of whether the bone mineral density of the vertebral body regions is abnormal is performed by a first classification model (e.g., the classification model 124). In some embodiments, when the bone mineral density of the vertebral body regions is abnormal, determination of whether the bone mineral density of the vertebral body regions belongs to osteopenia or osteoporosis based on the second set of features is performed by the second classification model (e.g., the classification model 125).

In some embodiments, the first classification model includes a SVM, Decision Tree, Random Forest model, or XGBoost model, etc. In some embodiments, the second classification model includes a SVM, Decision Tree, Random Forest model, or XGBoost model, etc.

In some embodiments, for each image, three histogram features and multiple textural features (including 9 gray-level co-occurrence matrix (GLCM) features, 13 gray-level run-length matrix (GLRLM) features, 14 gray-level size zone matrix (GLSZM) features, and 5 neighboring gray tone difference matrix (NGTDM) features) can be computed using MATLAB. These 44 features can be calculated for the region of interest (ROI) (e.g., the anterior part) in each image. In addition to these 44 features, some associated values of the radiodensity feature (e.g., an average value of the radiodensity feature in HU) can be calculated for the ROI (e.g., the anterior part) in each image. In some embodiments, the first set of features may correspond to one feature calculated from the first set of chest images, in which the one feature may be selected from these 44 or more features. The second set of features may be selected based on the first differential values, the gradient values (e.g., FIG. 8B), or the second differential values of the curved graph (e.g., FIG. 8A or 8C), which is generated based on the first set of features.

In operation 270, when the bone mineral density of the vertebral body regions is abnormal, a bone mineral density level is determined based on the second set of features. In some embodiments, when the bone mineral density of the vertebral body regions is normal, a bone mineral density level is determined based on the second set of features.

In some embodiments, the present disclosure may include one segmentation model and two classification models. Using the segmentation model and feature extraction, one set of features for one patient can be extracted or determined from the vertebral body region. That is, one set of features carries the information of the bone density of the one patient. The first classification model may be applied, based on the extracted features, to determine if the bone density of the patient belongs to normal class or abnormal class. If the bone density of the patient belongs to the abnormal class, the second classification model may be applied, based on the extracted features, to determine if the bone density of the patient belongs to osteopenia or osteoporosis. In operation 280, the bone mineral density level is output.

FIG. 3 is a flowchart of a method 3000 of processing a low-dose CT image, in accordance with some embodiments. The method 3000 can include operations 310, 320, 330, 340, 350, 360, 370, 380, and 390. In some embodiments, this method 3000 can be performed by one or more models. For example, the models can utilize artificial intelligence (AI). In some embodiments, a memory can store instructions, which may be executed by a processor to perform the method 3000. The method 3000 is similar to the method 2000 except for the operations 360 to 390.

In operation 350, a selected set of chest images are obtained or selected from the first set of chest images based on from the second set of features. The selected set of chest images may be obtained similarly to the reverse transform of the operation 240. The selected set of chest images may be obtained based on the Hounsfield unit of the second set of features.

The operation 370 determines whether a bone mineral density of the vertebral body regions is abnormal based on the selected set of chest images. In some embodiments, determination of whether the bone mineral density of the vertebral body regions is abnormal is performed by a first classification model (e.g., the classification model 124). In some embodiments, when the bone mineral density of the vertebral body regions is abnormal, determination of whether the bone mineral density of the vertebral body regions is the result of osteopenia or osteoporosis based on the selected set of chest images is performed by the second classification model (e.g., the classification model 125). In some embodiments, the first classification model includes a SVM, Decision Tree, Random Forest model, or XGBoost model, etc. In some embodiments, the second classification model includes a SVM, Decision Tree, Random Forest model, or XGBoost model, etc.

In some embodiments, for each image of the selected set of chest) images, three histogram features and multiple textural features (including 9 gray-level co-occurrence matrix (GLCM) features, 13 gray-level run-length matrix (GLRLM) features, 14 gray-level size zone matrix (GLSZM) features, and 5 neighboring gray tone difference matrix (NGTDM) features) can be computed using MAT-LAB. These 44 features can be calculated for the region of interest (ROI) (e.g., the anterior part) in each image of the selected set of chest images. In addition to these 44 features, some associated values of the radiodensity feature (e.g., an average value of the radiodensity feature in HU) can be calculated for the ROI (e.g., the anterior part) in each image. One or more features are calculated for the ROI in each image of the selected set of chest images. One vector consisting the one or more features can be obtained for each image of the selected set of chest images. In some embodiments, a total of 44 features are calculated for the ROI in each image of the selected set of chest images. One vector consisting the 44 features can be obtained for each image. In some embodiments, the selected set of chest images may include 40 to 60 LDCT chest images or slices for one patient, and the 40 to 60 corresponding vectors can be determined or calculated from the 40 to 60 LDCT chest images.

One vector of one image may contain one or more elements (or dimensions), in which one element (or dimension) corresponds to one feature mentioned above. In some embodiments, one vector of one image may contain 44 elements (or dimensions), in which one element (or dimension) corresponds to one feature mentioned above. In some embodiments, all vectors (e.g., 40-60 vectors) are averaged. An average vector of the all vectors is calculated dimension by dimension. In particular, the first element of the average vector is calculated based on the average of the first elements of the all vectors; the second element of the average vector is calculated based on the average of the second elements of the all vectors; and so on. In other words, the value of the first dimension of the average vector is calculated based on the average of the values of the first dimension of the all vectors; the value of the second dimension of the average vector is calculated based on the average of the values of the second dimension of the all vectors; and so on. After calculation, the average vector would be obtained. In some embodiments, the average vector contains 44 elements. That is, there are 44 dimensions in the average vector. Therefore, a total of 44 features are obtained and averaged over all LDCT images to represent the bone density features of the patient.

In some embodiments, in operation 370, the first classification model (e.g., the classification model 124) may be applied to the average vector of the selected set of chest images to determine whether a bone mineral density of the vertebral body regions is abnormal. When the bone mineral density of the vertebral body regions is abnormal, the second classification model (e.g., the classification model 125) may be applied to the average vector of the selected set of chest images to determine whether the bone mineral density of the vertebral body regions is the result of osteopenia or osteoporosis.

In operation 380, when the bone mineral density of the vertebral body regions is abnormal, a bone mineral density level is determined based on the selected set of chest images. In some embodiments, when the bone mineral density of the vertebral body regions is normal, a bone mineral density level is determined based on the selected set of chest images. In operation 390, the bone mineral density level is output.

In some embodiments, in operation 380, when the bone mineral density of the vertebral body regions is abnormal, a bone mineral density level is determined based on the average vector of the selected set of chest images. In some embodiments, when the bone mineral density of the vertebral body regions is normal, a bone mineral density level is determined based on the average vector of the selected set of chest images. In operation 390, the bone mineral density level is output.

Figure 4C:
FIGS. 4A, 4B, and 4C show low-dose CT images, in accordance with some embodiments.
Figure 4B:
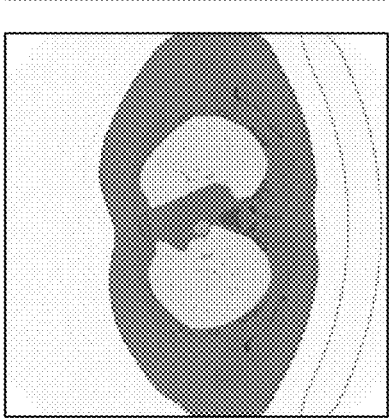
Figure 4A:

FIGS. 4A, 4B, and 4C show low-dose CT images, in accordance with some embodiments. Referring to FIG. 4A, the image is a chest image generated by a low-dose CT method. Referring to FIG. 4B, the semantic segmentation image is generated through the first segmentation model (e.g. the segmentation model 121). The semantic segmentation image includes lung, vertebral body (VB), heart, and other soft tissue areas. Referring to FIG. 4C, after avoiding involvement of the cortical bone and basivertebral veins, the vertebral body (VB) region of interest (ROI) (e.g., the central black portion) is obtained. An anterior part of the vertebral body is further defined or determined by the anterior ½ to ¾ of the vertebral body. In this way, the basivertebral veins and the cortical bone can be avoided.

FIGS. 5A, 5B, 5C, 6A, 6B, and 6C show low-dose CT images, in accordance with some embodiments. Referring to FIGS. 5A and 6A, the image is a chest image generated by a low-dose CT method. Referring to FIGS. 5B and 6B, the semantic segmentation image is generated through the first segmentation model. The semantic segmentation image includes lung, vertebral body (VB), heart, and other soft tissue areas. Referring to FIGS. 5C and 6C, after avoiding the involvement of the cortical bone and basivertebral veins, the vertebral body (VB) region of interest (ROI) (black) is obtained. An anterior part of the vertebral body is further defined or determined by the anterior ½ to ¾ of the vertebral body. In this way, the basivertebral veins and the cortical bone can be avoided. In some embodiments, a slice autoselection algorithm was developed to remove the slices (or images) located at the level of the apical lungs or the diaphragm (locations that often exhibit increased lordotic curvature of the spine or poor image quality, which can lead to suboptimal selection quality), where these slices (or images) exhibited a low ratio of the lung area to the vertebral body (VB) area (FIGS. 5A-5C and 6A-6C). In some embodiments, use of the 10th quantile as a threshold is effective for removing unwanted slices. FIGS. 5A-5C are the slices or images captured at the level of the apical lungs (upper). FIGS. 6A-6C are the slices or images captured at the level of diaphragm (lower). In some embodiments, the low-dose CT images may be captured at the level of apical lungs (upper) or the diaphragm (lower). These slices or images captured at the level of apical lungs (upper) or the diaphragm (lower) exhibit a low ratio of lung area to the VB area.

Figures 7A, 7B, 7C:
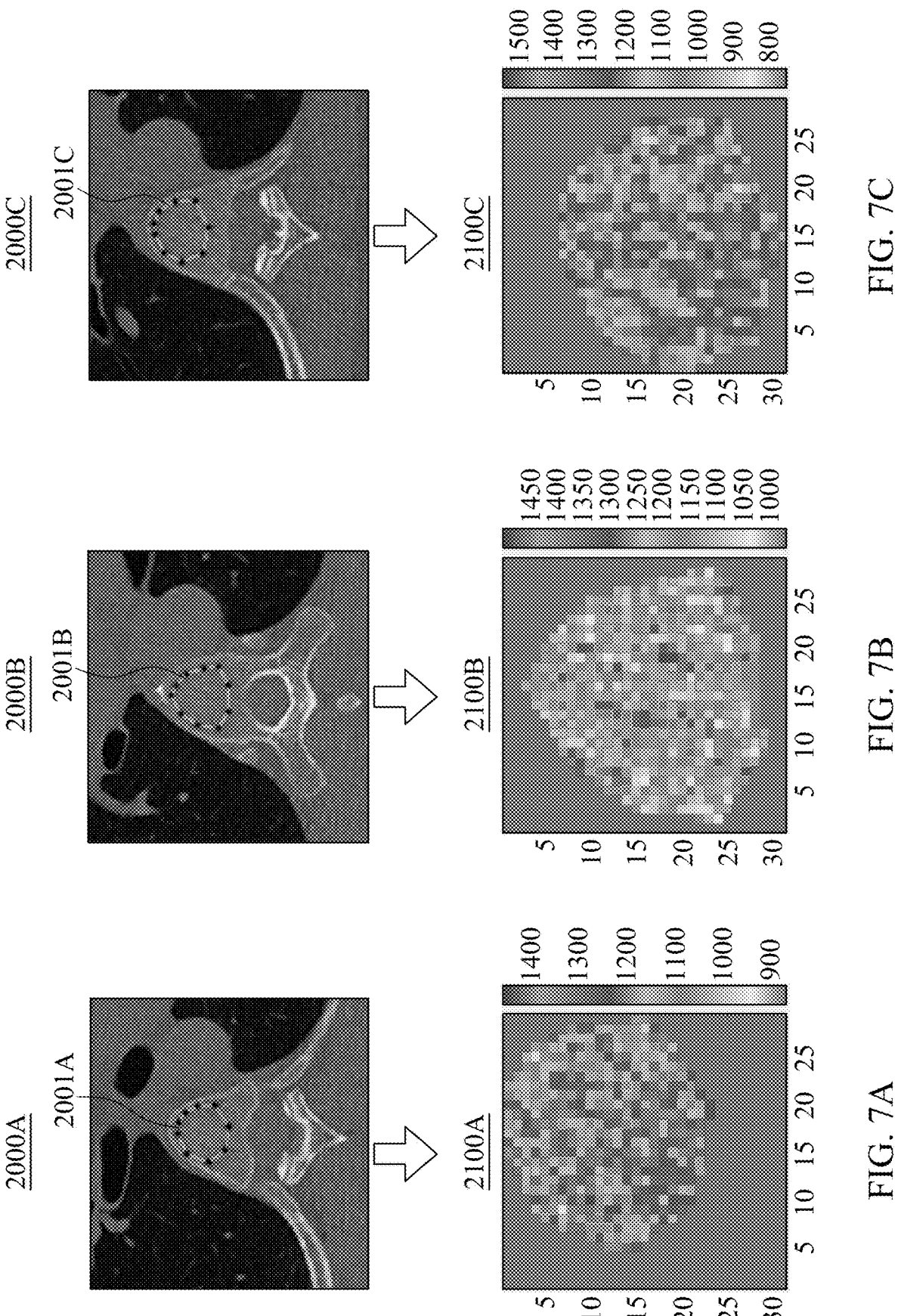
FIGS. 7A, 7B, and 7C show thoracic vertebrae images, in accordance with some embodiments.

FIGS. 7A, 7B, and 7C show thoracic vertebrae images, in accordance with some embodiments.

FIG. 7A shows an LDCT image 2000A and a bone feature image 2100A. The LDCT image 2000A can include an anterior part 2001A of the vertebral body. In some embodiments, the anterior part 2001A can be a part of the thoracic vertebra. The bone feature image 2100A can be obtained from the LDCT image 2000A. In some embodiments, the bone features can be extracted from the LDCT image 2000A. The bone features can be merely extracted from the region of interest (ROI) in the LDCT image 2000A (i.e., the anterior part 2001A). The gray scale in indicate different radiodensity values of the anterior part 2001A, and the radiodensity values can be presented in Hounsfield unit (HU).

FIG. 7B shows a LDCT image 2000B and a bone feature image 2100B. The LDCT image 2000B can include an anterior part 2001B of the vertebral body. In some embodiments, the anterior part 2001B can be a part of the thoracic vertebra. The bone feature image 2100B can be obtained from the LDCT image 2000B. In some embodiments, the bone features can be extracted from the LDCT image 2000B. The bone features can be merely extracted from the region of interest (ROI) in the LDCT image 2000B (i.e., the anterior part 2001B). The gray scale in indicate different radiodensity values of the anterior part 2001B, and the radiodensity values can be presented in Hounsfield unit (HU).

FIG. 7C shows a LDCT image 2000C and a bone feature image 2100C. The LDCT image 2000C can include an anterior part 2001C of the vertebral body. In some embodiments, the anterior part 2001C can be a part of the thoracic vertebrae. The bone feature image 2100C can be obtained from the LDCT image 2000C. In some embodiments, the bone features can be extracted from the LDCT image 2000C. The bone features can be merely extracted from the region of interest (ROI) in the LDCT image) 2000C (i.e., the anterior part 2001C). The gray scale in indicate different radiodensity values of the anterior part 2001C, and the radiodensity values can be presented in Hounsfield unit (HU).

FIGS. 8A, 8B, and 8C are diagrams obtained from the anterior parts of the first set of chest images, in accordance with some embodiments. Referring to FIG. 8A, a curved graph is obtained from the anterior parts of the first set of chest images. The y-axis of the curved graph (e.g., FIGS. 8A and 8C) may correspond to the first set of features. The x-axis of the curved graph (e.g., FIGS. 8A, 8B, and 8C) may correspond to the locations (or sequence) of slices (or CT images). In some embodiments, the y-axis of the curved graph may correspond to the radiodensity. The curved graph is determined based on a sequence (or locations) of the first set of chest images versus the first set of features of the anterior parts of the vertebral body regions of the first set of chest images. The radiodensity can be presented in Hounsfield unit (HU), which may be frequently used in CT scans. The Hounsfield unit of different material can be different. According to the different HU, it can be determined whether the bone region HU is in a normal range. In some embodiments, the bone mineral density of the vertebral body regions can be determined based on the HU of the bone regions.

Referring to FIG. 8B, the curved graph is obtained from the gradient of the curved graph in FIG. 8A. A sudden increase in the HU at the endplate (FIG. 8A) led to gradient oscillation, which revealed the opposing natures of the gradients between VBs (the middle portion (line) of FIG. 8B). The positive gradients at the endplates, negative gradients at the disc, and gradients close to zero in the trabecula helped us locate the endplate, disc, and trabecular slices. For this location process, the means and standard deviations (SDs) of all the gradients were calculated first. If the gradient difference from the two slices bilaterally adjacent to a certain central slice was higher than 1 SD (high oscillation), the central slice in question was regarded as an endplate slice or a disc slice and was excluded. The remaining slices were trabeculae (corresponding the segments with a lighter color in FIG. 8C). Based on this criterion and the vertical height of each patient's lungs, 70-90 image slices per LDCT scan were excluded. Referring to FIG. 8A, the mean HU (y-axis) across pixels in the VB ROI for each slice (x-axis). The endplates had higher HUs, whereas the intervertebral discs had lower HUs. Referring to FIG. 8B, the gradients calculated based on the VB ROI for each slice. Referring to FIG. 8C, the selection of the slice including the trabecular bone only, as indicated by the separated lines labeled as trabeculae.

Figure 9:
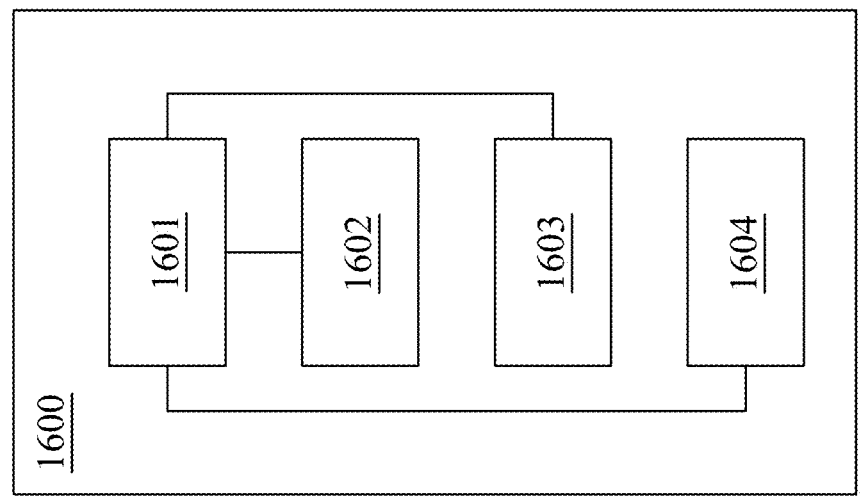
FIG. 9 is a schematic diagram of a computer device according to some embodiments of the present disclosure.

FIG. 9 is a schematic diagram showing a computer device 1600 according to some embodiments of the present disclosure. The computer device 1600 may be capable of performing one or more procedures, operations, or methods of the present disclosure. The computer device 1600 may be a server computer, a client computer, a personal computer (PC), a tablet PC, a set-top box (STB), a personal digital assistant (PDA), a cellular telephone, or a smartphone. The computing device 1600 comprises processor 1601, input/output interface 1602, communication interface 1603, and memory 1604. The input/output interface 1602 is coupled with the processor 1601. The input/output interface 1602 allows the user to manipulate the computing device 1600 to perform the procedures, operations, or methods of the present disclosure (e.g., the procedures, operations, or methods disclosed in FIGS. 2 and 3). The communication interface 1603 is coupled with the processor 1601. The communication interface 1603 allows the computing device 1600 to communicate with data outside the computing device 1600, for example, receiving data including images and/or any essential features. A memory 1604 may be a non-transitory computer readable storage medium. The memory 1604 is coupled with the processor 1601. The memory 1604 has stored program instructions that can be executed by one or more processors (for example, the processor 1601).

For example, upon execution of the program instructions stored on the memory 1604, the program instructions cause performance of the one or more procedures, operations, or methods disclosed in the present disclosure. For example, the program instructions may cause the computing device 1600 to perform, for example, receiving a first set of chest images generated by a low-dose CT method; determining, by the processor 1601, a vertebral body region in each image of the first set of chest images; determining, by the processor 1601, an anterior part within each vertebral body region; obtaining, by the processor 1601, a first set of features from the anterior parts of the first set of chest images; selecting, by the processor 1601, a second set of features from the first set of features; and determining, by the processor 1601, whether a bone mineral density of the vertebral body regions is abnormal based on the second set of features.

FIGS. 10A, 10B, and 10C show low-dose CT images, in accordance with some embodiments. FIG. 10A is a chest image generated by a low-dose CT method. Referring to FIG. 10B, the semantic segmentation image is generated by the first segmentation model (e.g., the segmentation model 121). The semantic segmentation image includes lung, vertebral body (VB), heart, and other soft tissue areas. Referring to FIG. 10C, after avoiding the involvement of the cortical bone and basivertebral veins, the vertebral body (VB) region of interest (ROI) (e.g., the central black portion) is obtained. An anterior part of the vertebral body is further defined or determined by the anterior ½ to ¾ of the vertebral body. In this way, the basivertebral veins and the cortical bone can be avoided. For LDCT, all the patients were scanned from the apical lung to the upper margin of the lumbar vertebrae on a dual-source CT scanner.

The segmentation task was framed as a four-class pixel-level classification problem, with one class for background and the other three classes for lungs, soft tissue, and verte-bral bodies (VBs). To address this problem, a residual CNN model may be employed based on ResNet50 architecture. Once the segmentation model had been developed, the LDCT images of all 197 patients were input into the developed model for automatic VB labeling. The number of labeled axial images per LDCT scan ranged from 270 to 320 slices based on the vertical height of each patient's lungs, which were used as a reference for thoracic vertebra selec-tion. The obtained segmentation masks were then upsampled to the original image resolution through nearest neighbor interpolation.

Next, a radiomic texture analysis is conducted with ROIs set within the central portion of the trabecular bones. These ROIs were obtained by removing pixels from the outer boundaries of segmented VBs by using an erosion algo-rithm. Subsequently, the anterior ½ to ¾ part of each VB was extracted to prevent involvement of the surrounding cortical bone or the basivertebral veins. Furthermore, a slice auto selection algorithm was applied to remove ROI slices if (1) the segmented VB ROIs transected the vertebral endplates or intervertebral discs or (2) the VB ROIs were positioned above the level of the apical lungs or below the diaphragm (locations that often exhibit increased lordotic curvature of the spine, leading to suboptimal ROI selection quality).

First, the ratio of the lung area to the VB area in each labeled LDCT image is calculated and 20 evenly spaced quantiles of these ratios are derived. Second, because lower ratios were obtained at the levels of the apical lung and the diaphragm, the images with ratios that did not exceed the threshold (10th quantile) are excluded. Third, the mean Hounsfield units (HUs) of each segmented VB ROI and their gradients were calculated to locate endplates and interver-tebral discs. Subsequently all images with large gradient changes were excluded. Finally, the histogram parameters of each segmented VB ROI, standard deviation (SD), skew-ness, and range were calculated. All images with histogram parameters more than twice the corresponding SD were excluded. Finally, 50 to 70 image slices per LDCT scan were selected for the subsequent development of the classification model.

The scope of the present disclosure is not intended to be limited to the particular embodiments of the process, machine, manufacture, and composition of matter, means, methods, steps, and operations described in the specifica-tion. As those skilled in the art will readily appreciate from the disclosure of the present disclosure, processes, machines, manufacture, composition of matter, means, methods, steps, or operations presently existing or later to be developed that perform substantially the same function or achieve substantially the same result as the corresponding embodiments described herein may be utilized according to the present disclosure. Accordingly, the appended claims are intended to include within their scope processes, machines, manufacture, and compositions of matter, means, methods, steps, or operations. In addition, each claim constitutes a separate embodiment, and the combination of various claims and embodiments are within the scope of the disclosure.

The methods, processes, or operations according to embodiments of the present disclosure can also be imple-mented on a programmed processor. However, the control-lers, flowcharts, and modules may also be implemented on a general purpose or special purpose computer, a pro-grammed microprocessor or microcontroller and peripheral integrated circuit elements, an integrated circuit, a hardware electronic or logic circuit such as a discrete element circuit, a programmable logic device, or the like. In general, any device on which resides a finite state machine capable of implementing the flowcharts shown in the figures may be used to implement the processor functions of the present disclosure.

An alternative embodiment preferably implements the methods, processes, or operations according to embodi-ments of the present disclosure on a non-transitory, com-puter-readable storage medium storing computer program-mable instructions. The instructions are preferably executed by computer-executable components preferably integrated with a network security system. The non-transitory, com-puter-readable storage medium may be stored on any suit-able computer readable media such as RAMs, ROMs, flash memory, EEPROMs, optical storage devices (CD or DVD), hard drives, floppy drives, or any suitable device. The computer-executable component is preferably a processor, but the instructions may alternatively or additionally be executed by any suitable dedicated hardware device. For example, an embodiment of the present disclosure provides a non-transitory, computer-readable storage medium having computer programmable instructions stored therein.

While the present disclosure has been described with specific embodiments thereof, it is evident that many alter-natives, modifications, and variations may be apparent to those skilled in the art. For example, various components of the embodiments may be interchanged, added, or substituted in the other embodiments. Also, all of the elements of each figure are not necessary for operation of the disclosed embodiments. For example, one of ordinary skill in the art of the disclosed embodiments would be able to make and use the teachings of the present disclosure by simply employing the elements of the independent claims. Accordingly, embodiments of the present disclosure as set forth herein are intended to be illustrative, not limiting. Various changes may be made without departing from the spirit and scope of the present disclosure.

Even though numerous characteristics and advantages of the present disclosure have been set forth in the foregoing description, together with details of the structure and func-tion of the invention, the disclosure is illustrative only. Changes may be made to details, especially in matters of shape, size, and arrangement of parts, within the principles of the invention to the full extent indicated by the broad general meaning of the terms in which the appended claims are expressed.

What is claimed is:

1. A method of processing a low-dose computed tomog-raphy (LDCT) chest image, comprising:

receiving a first set of chest images, the first set of chest images generated by a low-dose CT method;

determining a vertebral body region in each image of the first set of chest images;

determining an anterior part within each vertebral body region;

obtaining a first set of features from the anterior parts of the first set of chest images;

determining a curved graph based on a sequence of the first set of chest images versus the first set of features of the anterior parts of the vertebral body regions of the first set of chest images;

selecting a second set of features from the first set of features; and determining whether a bone mineral density of the vertebral body regions is abnormal based on the second set of features.

2. The method of claim 1, wherein whether the bone mineral density of the vertebral body regions is abnormal is determined by a first classification model.

3. The method of claim 2, further comprising:

when the bone mineral density of the vertebral body regions is abnormal, determination of whether the bone mineral density of the vertebral body regions belongs to osteopenia or osteoporosis by a second classification model.

4. The method of claim 1, wherein the vertebral body region in each of the first set of chest images is determined by a first segmentation model.

5. The method of claim 1, wherein the anterior part of the vertebral body region is determined by a second segmentation model.

6. The method of claim 1, wherein the vertebral body region includes thoracic spine, vertebral body, intervertebral disc, cortical bone, basivertebral vein, endplate, and trabecular bone.

7. The method of claim 6, wherein the anterior part of the vertebral body region includes the trabecular bone.

8. The method of claim 7, wherein the anterior part of the vertebral body region does not include the cortical bone and the basivertebral vein.

9. The method of claim 1, wherein the second set of features is selected by an anomaly detection model or a third classification model.

10. The method of claim 1, wherein the second set of features is selected based on first differential values or second differential values of the curved graph.

11. The method of claim 1, wherein the second set of features correspond to the anterior parts including a trabecular bone.

12. The method of claim 1, further comprising:

selecting a second subset of chest images from the first set of chest images, the second subset of chest images corresponding to the second set of features; and determining whether the bone mineral density of the vertebral body regions is abnormal based on the second subset of chest images.

13. The method of claim 12, further comprising:

determining a vector based on the second subset of chest images; and determining whether a bone mineral density of the vertebral body regions is abnormal based on the vector.

14. The method of claim 1, wherein, when the bone mineral density of the vertebral body regions is abnormal, the method further comprises:

determining a bone mineral density level based on the second set of features; and outputting the bone mineral density level.

15. The method of claim 1, wherein the anterior part of the vertebral body region is determined by shrinking an area of the vertebral body region in each of the first set of chest images.

16. The method of claim 15, wherein shrinking the area of the vertebral body region in each of the first set of chest images comprises shrinking 2 to 3 pixels from the boundary of the area of the vertebral body region.

17. The method of claim 1, wherein the second set of the features selected from the first set of features exclude a plurality of images, the plurality of images including an endplate and an intervertebral disc.

18. The method of claim 1, further comprising:

determining a lung region in each image of the first set of chest images;

for each image of the first set of chest images, determining a ratio of an area of the lung region to the whole image;

discarding images from the first set of chest images, in which each of the discarded images have the ratio smaller than a first threshold.

19. A device of processing a low-dose computed tomography (LDCT) chest image, comprising:

a processor; and a memory coupled with the processor, wherein the processor executes computer-readable instructions stored in the memory to perform operations, and the operations comprise:

receiving a first set of chest images, the first set of chest images generated by a low-dose CT method;

determining a vertebral body region in each image of the first set of chest images;

determining an anterior part within each vertebral body region;

obtaining a first set of features from the anterior parts of the first set of chest images;

determining a curved graph based on a sequence of the first set of chest images versus the first set of features of the anterior parts of the vertebral body regions of the first set of chest images;

selecting a second set of features from the first set of features; and determining whether a bone mineral density of the vertebral body regions is abnormal based on the second set of features.

* * * * *